(12) United States Patent
Liu et al.

(10) Patent No.: US 11,198,862 B2
(45) Date of Patent: *Dec. 14, 2021

(54) METHOD FOR PROMOTING ACETYLGLUCOSAMINE SYNTHESIS OF BACILLUS SUBTILIS

(71) Applicant: Jiangnan University, Wuxi (CN)

(72) Inventors: Long Liu, Wuxi (CN); Yang Gu, Wuxi (CN); Jieying Deng, Wuxi (CN); Jian Chen, Wuxi (CN); Guocheng Du, Wuxi (CN); Jianghua Li, Wuxi (CN)

(73) Assignee: Jiangnan University, Wuxi (CN)

( * ) Notice: Subject to any disclaimer, the term of this patent is extended or adjusted under 35 U.S.C. 154(b) by 114 days.

This patent is subject to a terminal disclaimer.

(21) Appl. No.: 16/299,319

(22) Filed: Mar. 12, 2019

(65) Prior Publication Data

US 2019/0309281 A1    Oct. 10, 2019

(30) Foreign Application Priority Data

Apr. 4, 2018  (CN) .......................... 201810299583.0

(51) Int. Cl.
*C12N 9/00*   (2006.01)
*C12N 9/02*   (2006.01)
*C12P 19/26*  (2006.01)

(52) U.S. Cl.
CPC ............. *C12N 9/93* (2013.01); *C12N 9/0008* (2013.01); *C12P 19/26* (2013.01); *C12Y 101/01037* (2013.01); *C12Y 101/01041* (2013.01); *C12Y 102/07001* (2013.01); *C12Y 102/07006* (2013.01); *C12Y 118/06001* (2013.01); *C12Y 604/01001* (2013.01)

(58) Field of Classification Search
CPC ...................................................... C12N 15/75
See application file for complete search history.

(56) References Cited

FOREIGN PATENT DOCUMENTS

CN    201610517961    * 11/2016

* cited by examiner

*Primary Examiner* — Suzanne M Noakes
(74) *Attorney, Agent, or Firm* — IPRO, PLLC; Na Xu

(57) ABSTRACT

The present invention relates to a method for promoting acetylglucosamine synthesis of *Bacillus subtilis*, which belongs to the field of genetic engineering. The present invention adopts the recombinant *Bacillus subtilis* BSGNKAP2 as a starting strain, exogenously introducing pyruvate carboxylase BalpycA derived from *Bacillus cereus*, eliminating the central carbon metabolism overflow of the *Bacillus subtilis* and avoiding the synthesis of the by-product acetoin; further, five exogenous reducing force metabolic reactions are introduced to replace the reaction of generating NADH in glycolysis pathway and tricarboxylic acid cycle to reconstruct intracellular reducing force metabolism, which specifically comprise glyceraldehyde-3-phosphate ferredoxin dehydrogenase, isocitrate $NAD^+$ dehydrogenase, a malate quinone dehydrogenase, a ketoacid ferredoxin oxidoreductase and a nitrogenase ferritin. In a shake-flask fermentation process using a complex medium, acetylglucosamine yield of the recombinant strain BSGNKAP8 is 24.50 g/L, acetylglucosamine/glucose yield is 0.469 g/g, respectively 1.97 times and 2.13 times of those of the starting strain BSGNKAP2.

9 Claims, 3 Drawing Sheets

Specification includes a Sequence Listing.

METHOD FOR PROMOTING ACETYLGLUCOSAMINE SYNTHESIS OF BACILLUS SUBTILIS

REFERENCE TO SEQUENCE LISTING

The instant application contains a Sequence Listing which has been submitted in ASCII format via EFS-Web and is hereby incorporated by reference in its entirety. Said ASCII Copy, created on May 3, 2021, is named "seq.txt" and is 32,915 bytes in size.

TECHNICAL FIELD

The present invention relates to a method for promoting acetylglucosamine synthesis of *Bacillus subtilis*, which belongs to the field of genetic engineering.

BACKGROUND

In human bodies, acetylglucosamine is a synthetic precursor of a glycosaminoglycan disaccharide unit, which plays an important role in repair and maintenance of cartilage and joint tissue function. Therefore, acetylglucosamine is widely added to medicines and nutritional diets to treat and repair joint damage. In addition, acetylglucosamine also has many applications in the fields of cosmetics and pharmacy. At present, acetylglucosamine is mainly produced by acid hydrolysis of chitin in shrimp shells or crab shells. However, waste liquid produced by the method pollutes the environment seriously, and the resulting products are apt to cause allergic reactions, being not suitable for people who are allergic to seafood.

*Bacillus subtilis* is widely used as a production host for food enzymic preparations and vital nutrient chemicals, and its products are certified as the Generally Regarded as Safe (GRAS) security level by FDA. The reaction formula for producing acetylglucosamine by fermentation of *Bacillus subtilis* is:

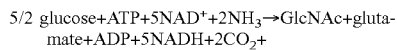

5/2 glucose+ATP+5NAD$^+$+2NH$_3$→GlcNAc+glutamate+ADP+5NADH+2CO$_2$+phosphate

The formula is obtained by calculating three precursors, namely 6-phosphate fructoses, acetyl coenzyme A and glutamine, of the de novo synthesis of acetylglucosamine, it can be seen from the formula that a large amount of NADH would be generated in the synthesis process of acetylglucosamine. The excessively generated NADH has a huge negative effect on the maximum theoretical yield (Yc) of the N-acetylglucosamine pathway. Due to the fact that cells need to maintain the balance of reduction force, the excessively generated NADH will be consumed in two ways: participating in the synthesis of other metabolites (resulting in the generation of by-products), and the other aspect being oxidized to produce ATP (causing a large amount of O$_2$ to be consumed during the fermentation process, and meanwhile, a large amount of bacterial cells is greatly produced). In addition, the use of *Bacillus subtilis* to synthesize acetylglucosamine is accompanied by metabolic overflow, resulting in the massive synthesis of by-product acetoin. Therefore, effectively treating the NADH concomitantly generated with the acetylglucosamine and the synthesis efficiency of the acetylglucosamine, meanwhile, avoiding the overflow of central carbon metabolism and improving the economical efficiency of carbon atoms, are urgent problems to be solved in the production of acetylglucosamine by the method of microbial fermentation.

SUMMARY

In order to solve the foregoing technical problem, the present invention provides a method for eliminating central carbon metabolism overflow of *Bacillus subtilis*, balancing intracellular reducing force and promoting acetylglucosamine synthesis, and the construction method exogenously introduces pyruvate carboxylase BalpycA derived from *Bacillus cereus*, eliminates the central carbon metabolism overflow of the *Bacillus subtilis* and avoids the synthesis of the by-product acetoin. Further, five exogenous reducing force metabolic reactions are introduced to replace the reaction of generating NADH in glycolysis pathway and tricarboxylic acid cycle to reconstruct intracellular reducing force metabolism, which specifically comprise glyceraldehyde-3-phosphate ferredoxin dehydrogenase, isocitrate NAD$^+$ dehydrogenase, a malate quinone dehydrogenase, a ketoacid ferredoxin oxidoreductase and a nitrogenase iron protein. The method is simple to operate and convenient to use, and the constructed recombinant *Bacillus subtilis* completely avoids central carbon metabolism so as to overflow and balance intracellular reducing power NADH metabolism.

The first objective of the present invention is to provide a recombinant strain of *Bacillus subtilis*, which integrates and expresses pyruvate carboxylase BalpycA, glyceraldehyde-3-phosphate ferredoxin dehydrogenase gor, isocitrate NAD$^+$ dehydrogenase icd, malate quinone dehydrogenase mqo, pyruvate ferredoxin oxidoreductase porAB and nitrogenase ferritin cyh.

In one embodiment of the present invention, the recombinant strain adopts *Bacillus subtilis* BSGNKAP2 as a starting strain, wherein the *Bacillus subtilis* BSGNKAP2 is disclosed in the patent application of No. CN201610517961.9.

In one embodiment of the present invention, the pyruvate carboxylase BalpycA is derived from *Bacillus cereus*, the pyruvate carboxylase BalpycA is shown as NCBI-Protein ID: AAS42897.1.

In one embodiment of the present invention, the pyruvate carboxylase BalpycA derived from *Bacillus cereus* is exogenously introduced, thus eliminating the central carbon metabolism overflow of the *Bacillus subtilis* and avoiding the synthesis of the by-product acetoin.

In one embodiment of the present invention, the pyruvate carboxylase BalpycA encoding gene balpycA is expressed by using a strong constitutive promoter P$_{43}$.

In one embodiment of the present invention, the pyruvate carboxylase BalpycA encoding gene balpycA is integrated into malS locus in *Bacillus subtilis* genome.

In one embodiment of the present invention, the glyceraldehyde-3-phosphate ferredoxin dehydrogenase is shown as NCBI-Protein ID: CAF30501.1, the isocitrate NAD$^+$ dehydrogenase is shown as NCBI-Protein ID: AKC61181.1, the malate quinone dehydrogenase is shown as NCBI-Protein ID:ADK05552.1, the pyruvate ferredoxin oxidoreductase porAB are shown as NCBI-Protein ID: ADK06337.1 and NCBI-Protein ID: ADK06336.1, and the nitrogenase iron protein is shown as NCBI-Protein ID: ACV00712.1.

In one embodiment of the present invention, the glyceraldehyde-3-phosphate ferredoxin dehydrogenase, the isocitrate NAD$^+$ dehydrogenase, the malate quinone dehydrogenase, pyruvate ferredoxin oxidoreductase and the nitrogenase iron protein is adopted to replace the reaction of generating NADH in glycolysis pathway and tricarboxylic acid cycle.

In one embodiment of the present invention, the glyceraldehyde-3-phosphate ferredoxin dehydrogenase encoding gene gor, the isocitrate NAD$^+$ dehydrogenase encoding gene icd, the malate quinone dehydrogenase encoding gene mqo, the pyruvate ferredoxin oxidoreductase encoding gene porAB and the nitrogenase iron protein gene cyh are expressed by using a strong constitutive promoter $P_{43}$ respectively.

In one embodiment of the present invention, the glyceraldehyde-3-phosphate ferredoxin dehydrogenase encoding gene gor, the isocitrate NAD$^+$ dehydrogenase encoding gene icd, the malate quinone dehydrogenase encoding gene mqo, the pyruvate ferredoxin oxidoreductase encoding gene porAB and the nitrogenase iron protein gene cyh are sequentially integrated into pyk, ywkA, kdgA, melA and pckA loci in *Bacillus subtilis* genome.

The second objective of the present invention is to provide a method for constructing the recombinant strain, comprising the following steps:

(1) constructing homologous recombination integration cassettes of the pyruvate carboxylase BalpycA encoding gene balpycA, the glyceraldehyde-3-phosphate ferredoxin dehydrogenase encoding gene gor, the isocitrate NAD$^+$ dehydrogenase encoding gene icd, the malate quinone dehydrogenase encoding gene mqo, the pyruvate ferredoxin oxidoreductase encoding gene porAB, and the nitrogenase iron protein encoding gene cyh of *Bacillus cereus*; and (2) integrating, by carrying out homologous recombination, the integration cassettes obtained in the step (1) into *Bacillus subtilis* genome.

In one embodiment of the present invention, upstream sequence (1000 bp) of the integration locus, zeocin resistant gene zeo sequence and strong constitutive promoter $P_{43}$, target gene sequence and upstream sequence (1000 bp) thereof are used for constructing an integration cassette in step (1).

In one embodiment of the present invention, the pyruvate carboxylase BalpycA encoding gene balpycA is derived from *Bacillus cereus*, and obtained by gene synthesis.

In one embodiment of the present invention, the glyceraldehyde-3-phosphate ferredoxin dehydrogenase encoding gene gor is derived from *Methanococcus maripaludis* KA1, obtained by gene synthesis, and subjected to codon optimization.

In one embodiment of the present invention, the isocitrate $NAD^+$ dehydrogenase encoding gene icd is derived from *Clostridium sporogenes*, obtained by gene synthesis, and subjected to codon optimization.

In one embodiment of the present invention, the malate quinone dehydrogenase encoding gene mqo is derived from *Bacillus cereus*, and obtained by gene synthesis.

In one embodiment of the present invention, the pyruvate ferredoxin oxidoreductase encoding gene porAB is derived from *Bacillus cereus*, obtained by gene synthesis, and subjected to codon optimization.

In one embodiment of the present invention, the nitrogenase iron protein encoding gene cyh is derived from *Cyanothece* sp. PCC 8802, obtained by gene synthesis, and subjected to codon optimization.

In one embodiment of the present invention, the pyruvate carboxylase BalpycA encoding gene balpycA derived from *Bacillus cereus* is integrated into malS locus in *Bacillus subtilis* genome.

In one embodiment of the present invention, the glyceraldehyde-3-phosphate ferredoxin dehydrogenase encoding gene gor is integrated into pyk locus in *Bacillus subtilis* genome.

In one embodiment of the present invention, the isocitrate $NAD^+$ dehydrogenase encoding gene icd is integrated into ywkA locus in *Bacillus subtilis* genome.

In one embodiment of the present invention, the malate quinone dehydrogenase encoding gene mqo is integrated into kdgA locus in *Bacillus subtilis* genome.

In one embodiment of the present invention, the pyruvate ferredoxin oxidoreductase encoding gene porAB is integrated into melA locus in *Bacillus subtilis* genome.

In one embodiment of the present invention, the nitrogenase iron protein encoding gene cyh is integrated into pckA locus in *Bacillus subtilis* genome.

The present invention also provides a method for preparing acetylglucosamine by the recombinant strain, comprising the following steps: activating the recombinant strain in a seed medium, then transferring activated seeds into a fermentation medium, adding an inducer to carry out fermentation culture and obtaining acetylglucosamine.

In one embodiment of the present invention, seeds are activated in the seed medium at 35-38° C., and activated seeds are fermented and cultured at 35-38° C.

In one embodiment of the present invention, the seed medium includes the following ingredients: peptone, yeast powder and sodium chloride.

In one embodiment of the present invention, the seed medium includes the following ingredients based on weight: 5-15 g/L of peptone, 5-10 g/L of yeast powder and 5-15 g/L of sodium chloride.

In one embodiment of the present invention, the fermentation medium includes the following ingredients: glucose, peptone, yeast powder, ammonium sulfate, dipotassium hydrogen phosphate, potassium dihydrogen phosphate, calcium carbonate, and a trace element solution.

In one embodiment of the present invention, the fermentation medium includes the following ingredients based on weight: 15-25 g/L of glucose, 5-8 g/L of peptone, 10-15 g/L of yeast powder, 5~8 g/L of ammonium sulfate, 10~15 g/L of dipotassium hydrogen phosphate, 2~3 g/L of potassium dihydrogen phosphate, 4~6 g/L of calcium carbonate, and 8~12 ml/L of trace element solution.

In one embodiment of the present invention, the trace element solution includes: manganese sulfate, cobalt chloride, sodium molybdate, zinc sulfate, aluminum chloride, copper chloride, boric acid and hydrochloric acid.

In one embodiment of the present invention, the trace element solution includes the following ingredients based on weight: 0.8-1.2 g/L of manganese sulfate, 0.2-0.6 g/L of cobalt chloride, 0.1-0.3 g/L of sodium molybdate, 0.1~0.3 g/L of zinc sulfate, 0.1~0.3 g/L of aluminum chloride, 0.1~0.3 g/L of copper chloride, 0.04~0.06 g/L of boric acid, and 3~8 mol/L of hydrochloric acid.

In one embodiment of the present invention, the activated seeds are transferred to the fermentation medium at an inoculum size of 5-15% for culture.

In one embodiment of the present invention, the inducer is xylose, and the dosage of xylose for per liter of fermentation medium is 5-10 g.

Compared with the prior art, the present invention has the following advantages:

The present invention provides a method for eliminating central carbon metabolism overflow of *Bacillus subtilis*, balancing intracellular reducing force, and promoting acetylglucosamine synthesis, and BSGNKAP8 is exogenously introduced pyruvate carboxylase BalpycA of *Bacillus cereus*, thus eliminating the central carbon metabolism overflow of the *Bacillus subtilis* and avoiding the synthesis of the by-product acetoin. Further, five exogenous reducing force metabolic reactions are introduced to replace the reaction of generating NADH in glycolysis pathway and tricarboxylic acid cycle to reconstruct intracellular reducing force metabolism, which specifically comprise glyceraldehyde-3-phosphate ferredoxin dehydrogenase, isocitrate $NAD^+$ dehydrogenase, a malate quinone dehydrogenase, a ketoacid ferredoxin oxidoreductase and a nitrogenase iron protein. Compared with the starting strain BSGNKAP2, the central carbon metabolism overflow is avoided and the synthesis of by-product acetoin is eliminated; meanwhile, in the process of producing acetylglucosamine, the intracellular NADH is effectively reduced, and at the same time, the acetylglucosamine synthesis is promoted. In a shake-flask fermentation process using a complex medium, acetylglucosamine yield of the recombinant strain BSGNKAP8 is 24.50 g/L, acetylglucosamine/glucose yield is 0.469 g/g, respectively 1.97 times and 2.13 times of those of the starting strain BSGNKAP2. The construction method of recombinant *Bacillus subtilis* of the present invention is simple and is convenient to use, and has a good application prospect.

BRIEF DESCRIPTION OF FIGURES

FIGS. 1A and 1B are a high performance liquid chromatography (HPLC) differential detection chromatogram for producing acetylglucosamine by fermenting *Bacillus subtilis*, in which, FIG. 1A shows HPLC detection results of BSGNKAP2 fermentation broth, and FIG. 1B shows HPLC detection results of BSGNKAP3 fermentation broth. The peaks of acetylglucosamine, acetoin and 2,3-butanediol have been marked.

DETAILED DESCRIPTION

Figure 1A:
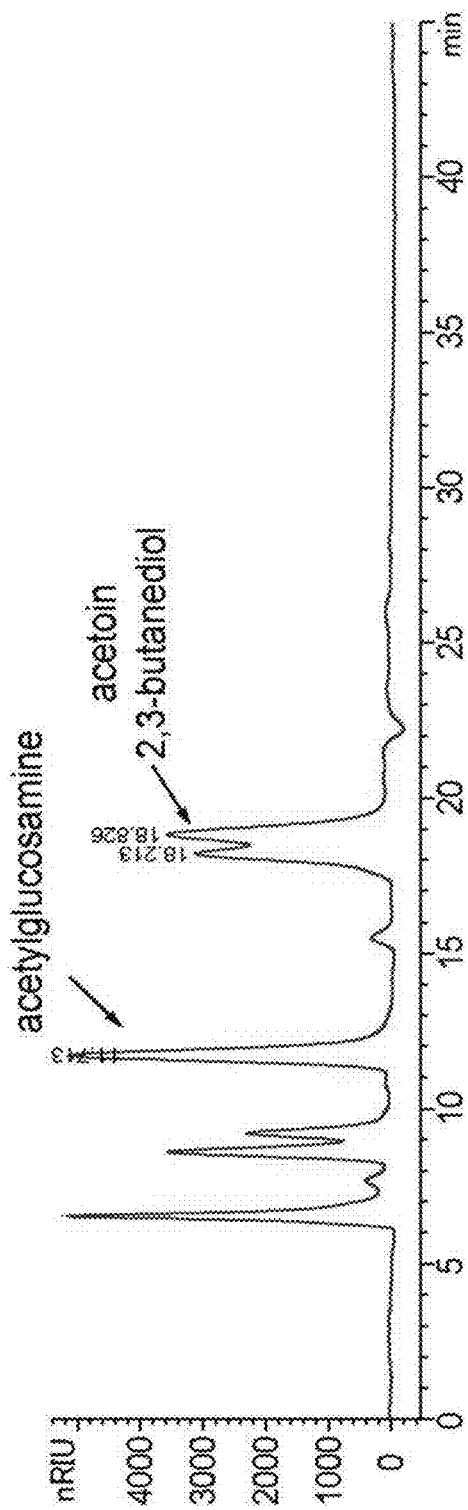

The technical solutions of the present invention are described in further detail below with reference to specific embodiments. The following embodiments are only for illustrating the present invention and are not intended to limit the scope of the present invention.

Example I: Construction of *Bacillus subtilis* BSGNKAP3

The *Bacillus subtilis* BSGNKAP2 is *B. subtilis* 168ΔnagPΔgamPΔgamAΔnagAΔnagBΔldhΔptaΔglcK ΔpckA Δpyk $P_{43}$-glmS P43-pycA::lox72, and GNA1 gene is freely expressed by using pP43NMK-GNA1 plasmid. Then, based on this, the pyruvate carboxylase BalpycA encoding gene balpycA (NCBI-Protein ID:AAS42897, SEQ ID NO:1) derived from *Bacillus cereus* is integrated into malS locus in *Bacillus subtilis* genome, further screening through zeocin resistance flat plates, carrying out colony PCR verification, sequencing and confirming integration to obtain the recombinant *Bacillus subtilis* BSGNKAP3.

Example II: Construction of *Bacillus subtilis* BSGNKAP4

*Bacillus subtilis* BSGNKAP3 is used as the host, and GNA1 gene is freely expressed by using pP43NMK-GNA1 plasmid. Then, based on this, the glyceraldehyde-3-phosphate ferredoxin dehydrogenase encoding gene gor (NCBI-ProteinID: CAF30501, SEQ ID NO:2) is integrated into pyk locus in *Bacillus subtilis* genome, further screening through zeocin resistance flat plates, carrying out colony PCR verification, sequencing and confirming integration to obtain the recombinant *Bacillus subtilis* BSGNKAP4.

Example III: Construction of Recombinant *Bacillus subtilis* BSGNKAP5

BSGNKAP4 is used as the host, and GNA1 gene is freely expressed by using pP43NMK-GNA1 plasmid. Then, based on this, the isocitrate $NAD^+$ dehydrogenase encoding gene icd (NCBI-Protein ID: AKC61181, SEQ ID NO:3) is integrated into ywkA locus in *Bacillus subtilis* genome, further screening through zeocin resistance flat plates, carrying out colony PCR verification, sequencing and confirming integration to obtain the recombinant *Bacillus subtilis* BSGNKAP5.

Example IV: Construction of Recombinant *Bacillus subtilis* BSGNKAP6

BSGNKAP5 is used as the host, and GNA1 gene is freely expressed by using pP43NMK-GNA1 plasmid. Then, based on this, the malate quinone dehydrogenase encoding gene mqo (NCBI-Protein ID: ADK05552, SEQ ID NO:4) is integrated into kdgA locus in *Bacillus subtilis* genome, further screening through zeocin resistance flat plates, carrying out colony PCR verification, sequencing and confirming integration to obtain the recombinant *Bacillus subtilis* BSGNKAP6.

Example V: Construction of Recombinant *Bacillus subtilis* BSGNKAP7

BSGNKAP6 is used as the host, and GNA1 gene is freely expressed by using pP43NMK-GNA1 plasmid. Then, based on this, the pyruvate ferredoxin oxidoreductase encoding genes porAB (NCBI-Protein ID: ADK06337, SEQ ID NO:5; and, NCBI-Protein ID: ADK06336, SEQ ID NO:6) are integrated into melA locus in *Bacillus subtilis* genome, further screening through zeocin resistance flat plates, carrying out colony PCR verification, sequencing and confirming integration to obtain the recombinant *Bacillus subtilis* BSGNKAP7.

Example VI: Construction of *Bacillus subtilis* BSGNKAP8

BSGNKAP7 is used as the host, and GNA1 gene is freely expressed by using pP43NMK-GNA1 plasmid. Then, based on this, the nitrogenase iron protein encoding gene cyh (NCBI-Protein ID: ACV00712, SEQ ID NO:7) is integrated into pckA locus in *Bacillus subtilis* genome, further screening through zeocin resistance flat plates, carrying out colony PCR verification, sequencing and confirming integration to obtain the recombinant *Bacillus subtilis* BSGNKAP8.

Example VII: Production of Acetylglucosamine by Fermenting Recombinant *Bacillus subtilis*

The ingredients of the seed medium include: 10 g/L of peptone, 5 g/L of yeast powder, and 10 g/L of sodium chloride.

The ingredients of the fermentation medium include: 20 g/L of glucose, 6 g/L of peptone, 12 g/L of yeast powder, 6 g/L of ammonium sulfate, 12.5 g/L of dipotassium hydrogen phosphate, 2.5 g/L of potassium dihydrogen phosphate, 5 g/L of calcium carbonate, and 10 ml/L of trace element solution.

The trace element solution includes the following ingredients based on weight: 1.0 g/L of manganese sulfate, 0.4 g/L of cobalt chloride, 0.2 g/L of sodium molybdate, 0.2 g/L of zinc sulfate, 0.1 g/L of aluminum chloride, 0.1 g/L of copper chloride, 0.05 g/L of boric acid, and 5 mol/L of hydrochloric acid.

High performance liquid chromatography is used for detecting content of acetylglucosamine. HPLC test conditions are as follows: instrument model Agilent 1200, RID detector, column: $NH_2$ column (250×4.6 mm, 5 μm), mobile phase: 70% acetonitrile, flow rate: 0.75 mL/min, column temperature: 30° C., and injection volume: 10 μL.

Detection of glucose concentration in fermentation broth: SBA Biosensor Analyzer.

Recombinant *Bacillus subtilis* BSGNKAP1 is cultured at the conditions of 37° C. and 220 rpm for 8 h in the seed medium, and then seed is transferred to the fermentation medium at the inoculum size of 5% and cultured at the conditions of 37° C. and 220 rpm for 48 h in a 500 ml shake flask. At the end of the fermentation, the content of acetylglucosamine in the fermentation supernatant will be measured.

Example IIX: Detection of Intracellular NADH of Recombinant *Bacillus subtilis*

The detection of intracellular NADH is performed by using the kits from Qingdao Jieshikang Biotechnology Co., Ltd. Collecting the thalluses in the logarithmic growth period into centrifuge tubes ($10^4$), adding alkaline extract volume (mL) to the ratio of 500-1000:1, performing ultrasonic crushing (ice bath, 20% or 200 W power, ultrasonic for 3 s, interval for 10 s, repeated for 30 times), performing water bath at 95° C. for 5 min (tightened to prevent water loss), and after cooling in ice bath, centrifuging at 10000 g and 4° C. for 10 min, adding 500 μl supernatant to 500 μl acidic extract to neutralize, uniformly mixing, centrifuging at 10000 g and 4° C. for 10 min, taking the supernatant, and placing the supernatant on the ice to detect NADH according to the standard kit procedures.

Figure 1B:
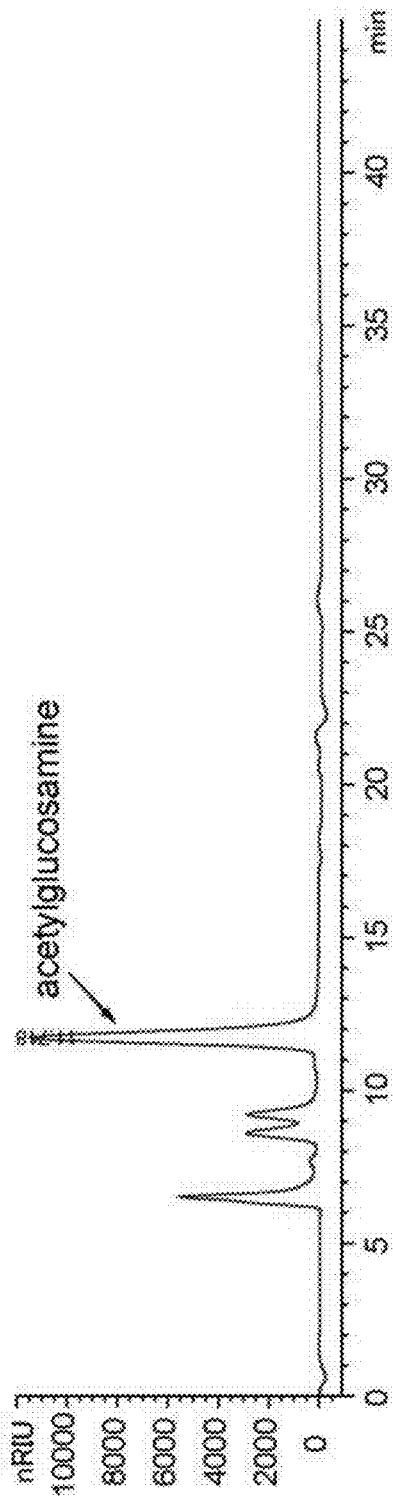
Figure 2:
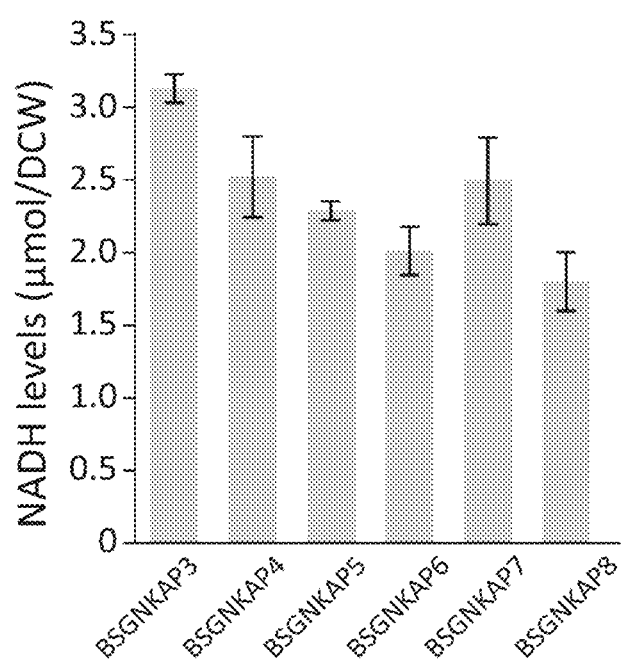
FIG. 2 shows the intracellular NADH levels of *Bacillus subtilis* engineered strains.

After shake-flask fermentation is completed, the acetylglucosamine yield of BSGNKAP8 is 24.50 g/L, and the acetylglucosamine/glucose yield is 0.469 g/g, respectively 1.97 times and 2.13 times of those of the starting strain BSGNKAP2 (as shown in FIG. 1), achieving an increase of the extracellular production of acetylglucosamine in the recombinant *Bacillus subtilis*. In addition, acetoin is completely eliminated (as shown in FIG. 1), and meanwhile, intracellular NADH levels of BSGNKAP3, BSGNKAP4, BSGNKAP5, BSGNKAP6, BSGNKAP7 and BSGNKAP8 are shown in FIG. 2. This strategy can completely avoid central carbon metabolism overflow, effectively avoid accumulation of intracellular reducing force NADH, and promote the synthesis of acetylglucosamine.

TABLE I

| | Comparison of acetylglucosamine and acetylglucosamine/glucose | | | | | | |
|---|---|---|---|---|---|---|---|
| Strain | BSGNKAP2 | BSGNKAP3 | BSGNKAP4 | BSGNKAP5 | BSGNKAP6 | BSGNKAP7 | BSGNKAP8 |
| Acetaminoglucose (g/L) | 12.4 ± 0.56 | 14.3 ± 0.28 | 17.5 ± 0.86 | 19.7 ± 1.11 | 18.1 ± 0.75 | 21.5 ± 0.44 | 24.5 ± 0.68 |
| Acetylglucosamine/glucose (g/g) | 0.22 ± 0.01 | 0.33 ± 0.01 | 0.35 ± 0.02 | 0.40 ± 0.02 | 0.42 ± 0.02 | 0.39 ± 0.01 | 0.47 ± 0.01 |

What is claimed is:

1. A recombinant strain of *Bacillus subtilis*, wherein the recombinant strain comprises an integrated expression sequence that expresses the following genes:
balpycA, which encodes pyruvate carboxylase BalpycA,
gor, which encodes a glyceraldehyde-3-phosphate ferredoxin dehydrogenase gor,
icd, which encodes an isocitrate $NAD^+$ dehydrogenase,
mqo, which encodes a malate quinone dehydrogenase,
porAB, which encodes a pyruvate ferredoxin oxidoreductase, and
cyh, which encodes a nitrogenase iron protein.

2. The recombinant strain according to claim 1, wherein the pyruvate carboxylase gene is from *Bacillus cereus*, and comprises the sequence SEQ ID NO:1.

3. The recombinant strain according to claim 1, wherein the balpycA gene is expressed under the control of a strong constitutive promoter $P_{43}$.

4. The recombinant strain according to claim 1, wherein the balpycA gene is integrated into a malS locus in a *Bacillus subtilis* genome of the recombinant strain.

5. The recombinant strain according to claim 1, wherein:

the glyceraldehyde-3-phosphate ferredoxin dehydrogenase peptide sequence encoded by the gor gene is SEQ ID NO:2, the isocitrate $NAD^+$ dehydrogenase peptide sequence encoded by the icd gene is SEQ ID NO:3, the malate quinone dehydrogenase peptide sequence encoded by the mqo gene is SEQ ID NO:4, the pyruvate ferredoxin oxidoreductase peptide sequence encoded by the porAB genes are SEQ ID NO:5 and SEQ ID NO:6, and the nitrogenase iron protein sequence encoded by the cyh gene is SEQ ID NO:7.

6. The recombinant strain according to claim 5, wherein: the gor gene, the icd gene, the mqo gene, the porAB gene, and the cyh gene, are expressed by a strong constitutive promoter $P_{43}$.

7. The recombinant strain according to claim 5, wherein the gor gene, the icd gene, the mqo gene, the porAB gene, and the cyh gene, are sequentially integrated into pyk, ywkA, kdgA, melA, and pckA loci in *Bacillus subtilis* genome, respectively.

8. A method manufacturing the recombinant strain according to claim 1, comprising the following steps:
(a) constructing homologous recombination integration cassettes of:

the pyruvate carboxylase BalpycA encoding gene balpycA, the glyceraldehyde-3-phosphate ferredoxin dehydrogenase encoding gene gor, the isocitrate NAD dehydrogenase encoding gene icd, the malate quinone dehydrogenase encoding gene mqo, the pyruvate ferredoxin oxidoreductase encoding gene porAB, and the nitrogenase iron protein encoding gene cyh of *Bacillus cereus*; and (b) integrating, by carrying out homologous recombination, the integration cassettes obtained in the step (a) into the *Bacillus subtilis* genome.

9. A method for preparing acetylglucosamine, which comprises:

activating the recombinant strain of claim 1 in a seed medium, transferring activated seeds into a fermentation medium, adding an inducer to induce expression from the integrated expression sequence, and fermenting at between 35 and 38° C. to obtain acetylglucosamine, wherein the seed medium comprises: peptone, yeast powder, and sodium chloride, and wherein the fermentation medium comprises: glucose, peptone, yeast powder, ammonium sulfate, dipotassium hydrogen phosphate, potassium dihydrogen phosphate, calcium carbonate, and a trace elements.

* * * * *

SEQUENCE LISTING

<160> NUMBER OF SEQ ID NOS: 7

<210> SEQ ID NO 1
<211> LENGTH: 1148
<212> TYPE: PRT
<213> ORGANISM: Bacillus cereus

<400> SEQUENCE: 1

```
Met Thr Lys Leu Gln Arg Ile Gln Lys Val Leu Val Ala Asn Arg Gly
1               5                   10                  15

Glu Ile Ala Ile Arg Val Phe Arg Ala Cys Ser Glu Leu Gly Leu Lys
            20                  25                  30

Thr Val Ala Ile Tyr Ser Lys Glu Asp Ser Gly Ser Tyr His Arg Tyr
        35                  40                  45

Lys Ala Asp Glu Ser Tyr Leu Val Gly Glu Gly Lys Lys Pro Ile Asp
    50                  55                  60

Ala Tyr Leu Asp Ile Glu Gly Ile Ile Glu Ile Ala Lys Ser Asn His
65                  70                  75                  80

Val Asp Ala Ile His Pro Gly Tyr Gly Phe Leu Ser Glu Asn Ile Gln
                85                  90                  95

Phe Ala Lys Arg Cys Glu Glu Glu Gly Ile Ile Phe Ile Gly Pro Lys
            100                 105                 110

Ser Lys His Leu Asp Met Phe Gly Asp Lys Val Lys Ala Arg Thr Gln
        115                 120                 125

Ala Gln Leu Ala Gln Ile Pro Val Ile Pro Gly Ser Asp Gly Pro Val
    130                 135                 140

Asp Ser Leu Glu Glu Val Glu Glu Phe Ala Glu Lys Tyr Asp Tyr Pro
145                 150                 155                 160

Ile Ile Ile Lys Ala Ser Leu Gly Gly Gly Gly Arg Gly Met Arg Ile
                165                 170                 175

Val Arg Thr Ser Glu Glu Leu Arg Glu Ser Tyr Asn Arg Ala Lys Ser
            180                 185                 190

Glu Ala Lys Ala Ala Phe Gly Asn Asp Glu Val Tyr Val Glu Lys Phe
        195                 200                 205

Val Glu Lys Pro Lys His Ile Glu Val Gln Ile Leu Ala Asp Glu Glu
    210                 215                 220

Gly Asn Val Val His Leu Tyr Glu Arg Asp Cys Ser Val Gln Arg Arg
225                 230                 235                 240

His Gln Lys Val Val Glu Ile Ala Pro Ser Val Ser Leu Ser Asp Asp
                245                 250                 255

Leu Arg Gln Arg Ile Cys Asp Ala Ala Val Lys Leu Thr Lys Asn Val
            260                 265                 270

Asn Tyr Leu Asn Ala Gly Thr Val Glu Phe Leu Val Lys Asp Asp Asn
        275                 280                 285

Phe Tyr Phe Ile Glu Val Asn Pro Arg Val Gln Val Glu His Thr Ile
    290                 295                 300

Thr Glu Met Ile Thr Gly Val Asp Ile Val Gln Ser Gln Ile Leu Ile
305                 310                 315                 320

Ala Asp Gly His Ala Leu His Ser Lys Leu Val Gly Val Pro Lys Gln
                325                 330                 335

Glu Glu Val Val Val His Gly Phe Ala Ile Gln Ser Arg Val Thr Thr
            340                 345                 350

Glu Asp Pro Leu Asn Asn Phe Met Pro Asp Thr Gly Lys Ile Met Ala
        355                 360                 365
```

Tyr Arg Ser Gly Gly Gly Phe Gly Val Arg Leu Asp Thr Gly Asn Ser
370                 375                 380

Phe Gln Gly Ala Val Ile Thr Pro Tyr Tyr Asp Ser Leu Leu Val Lys
385                 390                 395                 400

Val Thr Thr Trp Ala Leu Thr Phe Glu Gln Ala Ala Lys Met Glu
            405                 410                 415

Arg Asn Leu Lys Glu Phe Arg Ile Arg Gly Ile Lys Thr Asn Ile Pro
            420                 425                 430

Phe Leu Glu Asn Val Val Lys His Lys Asn Phe Leu Ser Gly Glu Tyr
            435                 440                 445

Asp Thr Ser Phe Ile Asp Ala Ser Pro Glu Leu Phe Leu Phe Ser Lys
450                 455                 460

Arg Lys Asp Arg Gly Thr Lys Met Leu Asn Tyr Ile Gly Thr Val Thr
465                 470                 475                 480

Val Asn Gly Phe Pro Gly Val Gly Lys Lys Glu Lys Pro Ile Phe Pro
                485                 490                 495

Asp Ala Arg Ile Pro Asn Val Leu His Ser Glu Pro Ile Gln Asn Gly
            500                 505                 510

Thr Lys Gln Ile Leu Asp Glu Arg Gly Ala Asp Gly Leu Val Lys Trp
            515                 520                 525

Val Gln Asp Gln Lys Arg Val Leu Leu Thr Asp Thr Thr Phe Arg Asp
530                 535                 540

Ala His Gln Ser Leu Leu Ala Thr Arg Ile Arg Thr Lys Asp Leu His
545                 550                 555                 560

Gln Ile Ala Glu Pro Thr Ala Arg Met Leu Pro Asn Leu Phe Ser Ala
                565                 570                 575

Glu Met Trp Gly Gly Ala Thr Phe Asp Val Ala Tyr Arg Phe Leu Lys
            580                 585                 590

Glu Asp Pro Trp Glu Arg Leu Leu Asp Leu Arg Glu Lys Met Pro Asn
            595                 600                 605

Val Leu Phe Gln Met Leu Leu Arg Ser Ser Asn Ala Val Gly Tyr Lys
610                 615                 620

Asn Tyr Pro Asp Asn Leu Ile Gln Lys Phe Val Glu Cys Ser Ala Gln
625                 630                 635                 640

Ala Gly Ile Asp Val Phe Arg Ile Phe Asp Ser Leu Asn Trp Val Glu
                645                 650                 655

Gly Met Arg Val Ala Ile Asp Ala Val Arg Asp Thr Gly Lys Ile Ala
            660                 665                 670

Glu Ala Thr Met Cys Tyr Thr Gly Asp Ile His Asp Pro Leu Arg Ser
            675                 680                 685

Lys Tyr Asp Leu Asn Tyr Tyr Lys Asn Leu Ala Lys Glu Leu Glu Ala
690                 695                 700

Ser Gly Ala His Ile Leu Gly Ile Lys Asp Met Ala Gly Leu Leu Lys
705                 710                 715                 720

Pro Asn Ala Ala Tyr Asp Leu Val Ser Ala Leu Lys Glu Thr Val Ser
                725                 730                 735

Ile Pro Ile His Leu His Thr His Asp Thr Ser Gly Asn Gly Ile Leu
            740                 745                 750

Thr Tyr Thr Lys Ala Ile Glu Ala Gly Val Asp Ile Val Asp Val Ala
            755                 760                 765

Val Ser Ser Met Ala Gly Gln Thr Ser Gln Pro Ser Ala Asn Thr Leu
770                 775                 780

Tyr Tyr Ala Leu Gly Gly Asn Glu Arg Gln Pro Asp Val Asn Ile Asp

```
                785                 790                 795                 800
Ser Leu Glu Lys Leu Ser His Tyr Trp Glu Asp Val Arg Lys Tyr Tyr
                    805                 810                 815
Ala Pro Phe Glu Ser Gly Met Asn Ala Pro His Thr Glu Val Tyr Met
                820                 825                 830
His Glu Met Pro Gly Gly Gln Tyr Ser Asn Leu Gln Gln Gln Ala Lys
                835                 840                 845
Ala Val Gly Leu Gly Asp Arg Phe Asp Glu Val Lys Val Met Tyr Arg
            850                 855                 860
Arg Val Asn Asp Met Phe Gly Asp Ile Val Lys Val Thr Pro Ser Ser
865                 870                 875                 880
Lys Val Val Gly Asp Met Ala Leu Phe Met Val Gln Asn His Leu Thr
                885                 890                 895
Glu Gln Asp Val Leu Glu Arg Gly His Ser Met Asp Phe Pro Gly Ser
                900                 905                 910
Val Val Glu Met Phe Ser Gly Asp Leu Gly Gln Pro Tyr Gly Gly Phe
            915                 920                 925
Pro Lys Lys Leu Gln Glu Ile Ile Leu Lys Gly Lys Glu Pro Leu Thr
        930                 935                 940
Val Arg Pro Gly Glu Leu Leu Glu Pro Val Asp Phe Asp Ala Leu Lys
945                 950                 955                 960
Glu Glu Leu Phe His Lys Leu Gly Arg Glu Val Thr Met Phe Asp Val
                965                 970                 975
Val Ala Tyr Ala Leu Tyr Pro Lys Val Phe Met Asp Tyr Glu Lys Val
            980                 985                 990
Ala Glu Ile Tyr Gly Asn Val Ser  Val Leu Asp Thr Pro  Thr Phe Phe
        995                 1000                 1005
Tyr Gly  Met Arg Leu Gly  Glu Ile Asp Val  Glu Ile Glu Gln
    1010                1015                1020
Gly Lys  Thr Leu Met Val Lys  Leu Val Ser Ile Gly  Glu Pro Gln
    1025                1030                1035
Pro Asp  Gly Asn Arg Val Leu  Tyr Leu Glu Phe Asn  Gly Gln Pro
    1040                1045                1050
Arg Glu  Ile Val Val Lys Asp  Glu Ser Val Lys Ala  Thr Val Ala
    1055                1060                1065
Gln Arg  Val Lys Gly Asn Arg  Glu Asn Pro Asn His  Ile Ser Ala
    1070                1075                1080
Thr Met  Pro Gly Thr Val Ile  Lys Val Val Val Lys  Glu Gly Asp
    1085                1090                1095
Glu Val  Lys Lys Gly Asp Ser  Met Ala Ile Thr Glu  Ala Met Lys
    1100                1105                1110
Met Glu  Thr Thr Val Gln Ala  Pro Phe Asn Gly Lys  Val Lys Lys
    1115                1120                1125
Val Tyr  Val Asn Asp Gly Asp  Ala Ile Gln Thr Gly  Asp Leu Leu
    1130                1135                1140
Ile Glu  Leu Asp His
    1145

<210> SEQ ID NO 2
<211> LENGTH: 613
<212> TYPE: PRT
<213> ORGANISM: Methanococcus maripaludis KA1

<400> SEQUENCE: 2
```

-continued

```
Met Asn Ile Leu Ile Asp Gly Ser Arg Gln Asn Tyr Glu Glu Leu Glu
 1               5                  10                  15

Glu Ser Glu Phe Pro Ile Ser Phe Gly Ile Asn Leu His Thr Lys Gln
             20                  25                  30

Glu Thr Trp Lys Tyr Asp Ala Phe Asp Glu Lys Asn Leu Phe Cys Phe
         35                  40                  45

Gly Lys Gly Ile Leu Pro Ile Ile Gly Gly His Arg Leu Ile Phe Ser
 50                  55                  60

Phe Arg Ser Pro Leu Trp Asp Gly Phe His Phe Ser Ala Met Gly Gly
 65                  70                  75                  80

Ala Gly Tyr Thr Phe Lys Asp Thr Gly Ile Gln Asn Val Ala Ile Thr
                 85                  90                  95

Gly Lys Cys Glu Val Pro Thr Val Ile Val Leu Asn Gly Glu Glu Asp
            100                 105                 110

Lys Leu Lys Ile Glu Phe Met Pro Phe Thr Glu Glu Ile Thr Asp Ile
            115                 120                 125

Tyr Glu Phe Asn Asp Lys Ile Ile Asp Leu Phe Lys Glu Lys Asn Tyr
        130                 135                 140

Arg Ala Phe Leu Val Gly Pro Ala Ser Lys Thr Thr Asn Met Gly Gly
145                 150                 155                 160

Ile Tyr Ser Gln Thr Ile Arg Asn Gly Lys Ile Val Glu Gly Ser Glu
                165                 170                 175

Asp Trp Ala Ala Arg Gly Gly Gly Ser Val Leu Tyr Gln Ala His
            180                 185                 190

Asn Val Leu Gly Val Val Phe Phe Gly Lys Lys Thr Pro Glu Lys Asn
        195                 200                 205

Leu Lys Glu Ile Val Glu Glu His Tyr Asn Lys Pro Tyr Thr Lys Val
210                 215                 220

Val Leu Glu His Thr Glu Lys Tyr Arg Tyr Ser Glu Glu Lys Lys Thr
225                 230                 235                 240

Gly Gly Thr Phe Gly Asn Asn Tyr His Val Thr Met Glu Leu Thr Pro
                245                 250                 255

Val Phe Asn Trp Arg Met Pro Phe Ile Asp Lys Asn Lys Arg Met Lys
            260                 265                 270

Leu His Lys Lys Ile Ile Glu Tyr Phe Val Asn Arg Phe Asp Glu Glu
        275                 280                 285

Ala Ile Glu Thr Lys Asn Trp Thr Asn Cys Gly Glu Pro Cys Pro Val
        290                 295                 300

Val Cys Lys Lys Tyr Arg Lys Gly Leu His Val Asp Tyr Glu Pro Tyr
305                 310                 315                 320

Glu Ala Asn Gly Pro Cys Ile Gly Val Phe Asp Ile Tyr Ala Ala Asp
                325                 330                 335

Lys Val Val His Thr Ile Asp Lys Leu Gly Phe Asp Ala Ile Glu Phe
            340                 345                 350

Gly Asn Leu Cys Ser Trp Thr Phe Glu Leu Leu Asp Asn Gly Met Leu
        355                 360                 365

Lys Pro Glu Glu Val Gly Ile Glu Lys Pro Val Phe Asp Ile Ser Asn
        370                 375                 380

Phe Glu Asn Asp Glu Asp Ile Leu Lys Asn Ser Met His Asn Ala Glu
385                 390                 395                 400

Gln Ala Val Lys Leu Ala Glu Ile Ile Ala Phe Gln Thr Asn Glu Phe
                405                 410                 415

Gly Lys Ile Cys Lys Ser Gly Thr Arg Arg Ala Gly Lys Ile Leu Asn
```

-continued

```
            420                 425                 430

Glu Lys Tyr Pro Asp Arg Ile Lys Asp Lys Lys Phe Glu Asp Phe Gly
        435                 440                 445

Val Tyr Asp Ser Phe Gly Glu Arg Gly Gln Ile Ser Pro Thr Met Tyr
    450                 455                 460

Trp Ala Ile Gly Asn Phe Met Pro Tyr Leu Ile Gln Gly Lys Tyr Leu
465                 470                 475                 480

Thr His Tyr Gln Cys Gly Val Phe Leu Glu Pro Glu Glu Leu Ala Glu
                485                 490                 495

Leu Ser Val Lys Asn Ser Ile Glu Glu Ile Thr Leu Glu Asn Leu Gly
            500                 505                 510

Ile Cys Arg Phe His Arg Lys Trp Val Thr Pro Ile Ile Glu Lys Leu
        515                 520                 525

Val Lys Glu Met Ser Asp Val Asn Leu Asn Glu Glu Ser Met Glu Leu
    530                 535                 540

Phe Lys Lys Ile Ala Lys Tyr Asp Ser Asn Ile Gly Cys Pro Glu Met
545                 550                 555                 560

Glu Ser Glu Arg Val Lys Glu Leu Ile Ile Ala Gly Ala Phe Glu Phe
                565                 570                 575

Glu Asn Glu Lys Trp Ser Lys Glu Phe Glu Asn Gly Asn Phe Asp Glu
            580                 585                 590

Tyr Ile Lys Arg Val Leu Glu Lys Tyr Ser Glu Leu Leu Glu Ile Asp
        595                 600                 605

Trp Lys Leu Lys Glu
    610

<210> SEQ ID NO 3
<211> LENGTH: 332
<212> TYPE: PRT
<213> ORGANISM: Clostridium sporogenes

<400> SEQUENCE: 3

Met Lys His Asn Ile Thr Leu Ile Pro Gly Asp Gly Ile Gly Pro Glu
1               5                   10                  15

Val Thr Glu Ala Ala Arg Lys Val Ile Asp Ala Val Gly Val Asp Ile
            20                  25                  30

Asn Trp His Val Val Glu Ala Gly Glu Lys Val Leu Asp Lys Tyr Gly
        35                  40                  45

Thr Pro Leu Pro His Tyr Val Leu Asp Ser Ile Lys Glu Asn Lys Val
    50                  55                  60

Ala Leu Lys Gly Pro Val Thr Thr Pro Val Gly Lys Gly Phe Arg Ser
65                  70                  75                  80

Val Asn Val Thr Leu Arg Lys Ser Leu Asn Leu Tyr Ala Asn Ile Arg
                85                  90                  95

Pro Val Lys Ser Tyr Lys Gly Ile Lys Ser Arg Tyr Glu Asn Val Asp
            100                 105                 110

Leu Ile Ile Val Arg Glu Asn Thr Glu Asp Leu Tyr Ala Gly Ile Glu
        115                 120                 125

His Met Ile Gly Asp Asp Ile Ala Glu Ser Ile Lys Val Ile Thr Lys
    130                 135                 140

Lys Ala Ser Asp Arg Ile Val Glu Tyr Ala Phe Asn Leu Ala Lys Glu
145                 150                 155                 160

Glu Asn Arg Asn Lys Val Thr Ala Val His Lys Ala Asn Ile Met Lys
                165                 170                 175
```

```
Leu Ser Asp Gly Leu Phe Leu Lys Cys Ala Lys Lys Ile Ala Ser Arg
            180                 185                 190

Asn Gln Asp Val Asn Phe Glu Asp Val Ile Val Asp Ala Met Ala Met
        195                 200                 205

Lys Leu Val Leu Asn Pro Glu Lys Tyr Asp Val Leu Val Met Pro Asn
    210                 215                 220

Leu Tyr Gly Asp Ile Leu Ser Asp Met Ala Ala Gly Leu Val Gly Gly
225                 230                 235                 240

Leu Gly Leu Leu Pro Gly Ala Asn Ile Gly His Lys Gly Ala Val Phe
                245                 250                 255

Glu Ala Ala His Gly Ala Ala Pro Asp Ile Ala Gly Lys Asn Lys Ala
            260                 265                 270

Asn Pro Thr Ala Cys Ile Leu Ser Gly Ala Met Met Leu Lys Tyr Ile
        275                 280                 285

Gly Glu Asn Glu Lys Ala Lys Lys Ile Glu Asn Ala Ile Ala Lys Val
    290                 295                 300

Phe Ile Asp Gly Lys Tyr Leu Thr Glu Asp Leu Gly Gly Asn Ser Thr
305                 310                 315                 320

Thr Glu Glu Phe Thr Glu Ala Val Ile Gly Asn Leu
                325                 330

<210> SEQ ID NO 4
<211> LENGTH: 500
<212> TYPE: PRT
<213> ORGANISM: Bacillus cereus

<400> SEQUENCE: 4

Met Ser Asn Met Gln Gln Lys Thr Asp Val Ile Leu Ile Gly Ala Gly
1               5                   10                  15

Ile Met Ser Ala Thr Leu Gly Ser Leu Leu Lys Glu Leu Ala Pro Glu
            20                  25                  30

Trp Glu Ile Lys Val Phe Glu Lys Leu Ala Ser Ala Gly Glu Glu Ser
        35                  40                  45

Ser Asn Glu Trp Asn Asn Ala Gly Thr Gly His Ser Ala Leu Cys Glu
    50                  55                  60

Leu Asn Tyr Thr Ser Glu Lys Ser Asp Gly Ser Ile Asp Ile Ser Lys
65                  70                  75                  80

Ala Val Lys Val Asn Glu Gln Phe Gln Leu Ser Arg Gln Phe Trp Ala
                85                  90                  95

Tyr Leu Val Lys Ser Lys Leu Ile Arg Asn Pro Gln Asp Phe Ile Met
            100                 105                 110

Pro Leu Pro His Met Ser Leu Val Gln Gly Glu Lys Asn Val Glu Phe
        115                 120                 125

Leu Lys Asn Arg Phe Glu Ala Leu Ser Lys Asn Pro Leu Phe Gln Gly
    130                 135                 140

Met Glu Phe Ser Asp Ala Pro Glu Thr Leu Lys Lys Trp Leu Pro Leu
145                 150                 155                 160

Ile Met Glu Gly Arg Thr Ser Asn Glu Pro Met Ala Ala Thr Lys Ile
                165                 170                 175

Asp Ser Gly Thr Asp Val Asn Phe Gly Ala Leu Thr Arg Met Leu Phe
            180                 185                 190

Asp Tyr Leu Lys Thr Lys Asp Val Glu Leu Asn Tyr Lys His Ser Val
        195                 200                 205

Glu Asn Ile Lys Arg Thr Lys Asn Gly Leu Trp Glu Val Lys Val His
    210                 215                 220
```

Asp Met Asn Ser Gly Lys Ile Glu His His Thr Ala Lys Phe Val Phe
225                 230                 235                 240

Ile Gly Gly Gly Gly Ser Leu Pro Leu Leu Gln Lys Thr Gly Ile
            245                 250                 255

Pro Glu Ser Lys His Ile Gly Gly Phe Pro Val Ser Gly Leu Phe Met
            260                 265                 270

Val Cys Lys Asn Gln Lys Val Val Glu Gln His His Ala Lys Val Tyr
                275                 280                 285

Gly Lys Ala Lys Val Gly Ala Pro Pro Met Ser Val Pro His Leu Asp
                290                 295                 300

Thr Arg Tyr Ile Asp Asn Lys Lys Ala Leu Leu Phe Gly Pro Phe Ala
305                 310                 315                 320

Gly Phe Ser Pro Lys Phe Leu Lys Thr Gly Ser Asn Leu Asp Leu Ile
                325                 330                 335

Gly Ser Val Lys Pro Asn Asn Val Leu Thr Met Leu Ala Ala Gly Val
            340                 345                 350

Lys Glu Met Gly Leu Thr Lys Tyr Leu Ile Gln Gln Val Met Leu Ser
            355                 360                 365

His Glu Lys Arg Met Glu Glu Leu Arg Glu Phe Ile Pro Asn Ala Lys
            370                 375                 380

Ser Glu Asp Trp Asp Ile Val Val Ala Gly Gln Arg Val Gln Val Ile
385                 390                 395                 400

Lys Asp Thr Asp Ala Gly Gly Lys Gly Thr Leu Gln Phe Gly Thr Glu
                405                 410                 415

Val Val Ser Ala Ala Asp Gly Ser Ile Ala Ala Leu Leu Gly Ala Ser
                420                 425                 430

Pro Gly Ala Ser Thr Ala Val His Val Met Leu Glu Val Leu Glu Lys
            435                 440                 445

Cys Phe Pro Ser Arg Met Val Glu Trp Glu Gly Lys Ile Lys Glu Met
            450                 455                 460

Ile Pro Ser Tyr Gly Ile Ser Leu Thr Glu Asn Pro Arg Leu Phe Gln
465                 470                 475                 480

Asp Leu His Thr Ser Thr Gly Arg Thr Leu Gly Leu Asn Glu Lys Glu
                485                 490                 495

Thr Val His Asn
            500

<210> SEQ ID NO 5
<211> LENGTH: 585
<212> TYPE: PRT
<213> ORGANISM: Bacillus cereus

<400> SEQUENCE: 5

Met Ile Ser Gln Leu Ser Trp Lys Val Gly Gly Gln Gly Glu Gly
1               5                   10                  15

Ile Glu Ser Thr Gly Ile Phe Cys Ile Ala Leu Asn Arg Leu Gly
            20                  25                  30

Tyr Tyr Leu Tyr Gly Tyr Arg His Phe Ser Ser Arg Ile Lys Gly Gly
            35                  40                  45

His Thr Asn Asn Lys Ile Arg Val Ser Thr Thr Glu Val Arg Ala Ile
50 55 60

Ser Asp Asp Leu Asp Ile Leu Ile Ala Phe Asp Gln Glu Thr Ile Asp
65 70 75 80

Phe Asn Phe His Glu Leu Arg Pro Gly Gly Ile Val Val Ala Asp Ala

```
            85                  90                  95
Lys Phe Asn Pro Thr Ile Pro Asp Asn Thr Asp Val Asn Leu Tyr Val
            100                 105                 110

Ile Pro Phe Thr Asp Ile Ala Ser Glu Leu Gly Thr Ser Leu Met Lys
            115                 120                 125

Asn Met Val Ala Val Gly Ala Ser Ser Ala Val Leu Gly Leu Asp Glu
    130                 135                 140

Thr Ala Tyr Leu Asp Val Val Glu Glu Ile Phe Gly Arg Lys Gly Glu
145                 150                 155                 160

Gln Val Val Gln Lys Asn Met Asp Ala Ile Lys Arg Gly Ser Gln Tyr
                165                 170                 175

Met Lys Glu Leu Leu Gly Glu Lys Val Asn Met Met Gln Leu Glu Lys
            180                 185                 190

Ala Asp Gly Gln Lys Arg Met Phe Met Ile Gly Asn Asp Ala Ile Ala
                195                 200                 205

Phe Gly Ala Val Ala Gly Gly Ala Arg Phe Met Ser Ala Tyr Pro Ile
        210                 215                 220

Thr Pro Ala Ser Glu Ile Met Glu Tyr Leu Ile Lys Lys Leu Pro Lys
225                 230                 235                 240

Val Gly Gly Thr Val Ile Gln Thr Glu Asp Glu Ile Ala Ala Cys Thr
                245                 250                 255

Met Ala Ile Gly Ala Asn Tyr Ala Gly Val Arg Thr Leu Thr Ala Ser
            260                 265                 270

Ala Gly Pro Gly Leu Ser Leu Met Met Glu Ala Ile Gly Leu Ala Gly
        275                 280                 285

Ile Thr Glu Thr Pro Leu Val Ile Val Asp Thr Gln Arg Gly Gly Pro
        290                 295                 300

Ser Thr Gly Leu Pro Thr Lys Gln Glu Gln Ser Asp Leu Met Ala Met
305                 310                 315                 320

Ile Tyr Gly Thr His Gly Glu Ile Pro Lys Ile Val Met Ala Pro Ser
                325                 330                 335

Thr Val Glu Glu Ala Phe Tyr Asp Ile Val Glu Ala Phe Asn Leu Ser
            340                 345                 350

Glu Glu Tyr Gln Val Pro Val Ile Phe Leu Thr Asp Leu Gln Leu Ser
        355                 360                 365

Leu Gly Lys Gln Thr Val Glu Pro Leu Lys Leu Asp Lys Val Glu Ile
        370                 375                 380

Arg Arg Gly Lys Leu Asp Leu Glu Ala Glu Leu Pro Glu Arg Glu Asn
385                 390                 395                 400

Lys Ala Tyr Phe Lys Arg Tyr Glu Val Thr Glu Asp Gly Val Ser Pro
                405                 410                 415

Arg Val Leu Pro Gly Met Lys Asn Gly Val His His Val Thr Gly Val
                420                 425                 430

Glu His Asp Glu Thr Gly Lys Pro Ser Glu Ser Ala Leu Asn Arg Lys
            435                 440                 445

Asp Gln Met Asp Lys Arg Phe Arg Lys Met Glu Asn Leu Lys Phe Asn
    450                 455                 460

Thr Pro Val Tyr Lys Asn Val Lys His Glu Glu Ala Asp Val Leu Leu
465                 470                 475                 480

Val Gly Phe Asn Ser Thr Arg Gly Ala Ile Glu Glu Ala Met Glu Arg
                485                 490                 495

Leu Glu Gln Glu Gly Met Lys Val Asn His Ala His Val Arg Leu Ile
            500                 505                 510
```

-continued

```
His Pro Phe Pro Thr Ala Glu Ile Asp Pro Leu Val Lys Lys Ala Lys
        515                 520                 525

Arg Val Val Val Val Glu Asn Asn Ala Thr Gly Gln Leu Ala Asn Ile
    530                 535                 540

Met Lys Met Asn Leu Gly Asn Gly Glu Lys Ile Ser Ser Leu Leu Lys
545                 550                 555                 560

Tyr Asp Gly Asn Pro Phe Leu Pro Lys Glu Ile Tyr Asn Glu Cys Lys
                565                 570                 575

Lys Gly Val Val Leu Asn Gly Asn Ile
            580                 585

<210> SEQ ID NO 6
<211> LENGTH: 288
<212> TYPE: PRT
<213> ORGANISM: Bacillus cereus

<400> SEQUENCE: 6

Met Ala Thr Phe Lys Asp Phe Arg Asn Ser Val Lys Pro Asn Trp Cys
1               5                   10                  15

Pro Gly Cys Gly Asp Phe Ser Val Gln Ala Ala Ile Gln Arg Ala Ala
            20                  25                  30

Ala Asn Val Gly Leu Asn Pro Asp Glu Leu Ala Val Ile Ser Gly Ile
        35                  40                  45

Gly Cys Ser Gly Arg Ile Ser Gly Tyr Ile Asn Ser Tyr Gly Val His
    50                  55                  60

Ser Ile His Gly Arg Ala Leu Pro Ile Ala Gln Gly Val Lys Met Ala
65                  70                  75                  80

Asn Arg Asp Leu Thr Val Ile Ala Ser Gly Gly Asp Gly Asp Gly Phe
                85                  90                  95

Ala Ile Gly Met Gly His Thr Ile His Ser Ile Arg Arg Asn Ile Asp
            100                 105                 110

Ile Thr Tyr Ile Val Met Asp Asn Gln Ile Tyr Gly Leu Thr Lys Gly
        115                 120                 125

Gln Thr Ser Pro Arg Ser Glu Ala Gly Phe Lys Thr Lys Ser Thr Pro
    130                 135                 140

Gln Gly Ser Ile Glu Pro Ser Leu Asn Val Met Glu Met Ala Leu Thr
145                 150                 155                 160

Ala Gly Ala Thr Phe Val Ala Gln Ser Phe Ser Ser Asp Leu Lys Glu
                165                 170                 175

Leu Thr Gln Ile Ile Glu Ala Gly Ile Asn His Lys Gly Phe Ser Leu
            180                 185                 190

Ile Asn Val Phe Ser Pro Cys Val Thr Tyr Asn Lys Val Asn Thr Tyr
        195                 200                 205

Asp Trp Phe Lys Glu Asn Leu Thr Lys Leu Ser Thr Val Glu Gly Tyr
    210                 215                 220

Asp Pro Ser Asn Arg Met Met Ala Met Gln Thr Leu Met Glu Asn Asn
225                 230                 235                 240

Gly Leu Val Thr Gly Leu Ile Tyr Gln Asn Thr Ala Gln Pro Ser Tyr
                245                 250                 255

Gln Glu Leu Val Lys Gly Tyr Ser Glu Lys Pro Leu Val Gln Ser Asp
            260                 265                 270

Leu Asn Met Asp Gln Lys Met Phe Asp Glu Leu Val Ala Glu Phe Met
        275                 280                 285
```

```
<210> SEQ ID NO 7
<211> LENGTH: 296
<212> TYPE: PRT
<213> ORGANISM: Cyanothece sp. PCC 8802

<400> SEQUENCE: 7

Met Arg Gln Ile Ala Phe Tyr Gly Lys Gly Gly Ile Gly Lys Ser Thr
1               5                   10                  15

Thr Ser Gln Asn Thr Leu Ala Gly Met Ala Gln Ala Gly Asn Arg Ile
            20                  25                  30

Met Ile Val Gly Cys Asp Pro Lys Ala Asp Ser Thr Arg Leu Ile Leu
        35                  40                  45

Asn Cys Lys Ala Gln Val Thr Val Leu His Leu Ala Ala Glu Arg Gly
50                  55                  60

Ala Val Glu Asp Leu Glu Leu Ser Asp Val Leu Leu Thr Gly Phe Glu
65                  70                  75                  80

Asn Ile Lys Cys Val Glu Ser Gly Gly Pro Glu Pro Gly Val Gly Cys
                85                  90                  95

Ala Gly Arg Gly Ile Ile Thr Ser Ile Asn Phe Leu Glu Glu Glu Gly
            100                 105                 110

Ala Tyr Glu Asp Leu Asp Phe Val Ser Tyr Asp Val Leu Gly Asp Val
        115                 120                 125

Val Cys Gly Gly Phe Ala Met Pro Ile Arg Glu Gly Lys Ala Gln Glu
130                 135                 140

Ile Tyr Ile Val Thr Ser Gly Glu Met Met Ala Met Tyr Ala Ala Asn
145                 150                 155                 160

Asn Ile Ala Arg Gly Ile Leu Lys Tyr Ala His Thr Gly Gly Val Arg
                165                 170                 175

Leu Gly Gly Leu Ile Cys Asn Ser Arg Asn Val Asn Lys Glu Ile Glu
            180                 185                 190

Leu Ile Glu Glu Leu Ala Glu Arg Leu Asn Thr Gln Met Ile His Phe
        195                 200                 205

Val Pro Arg Ser Lys Gln Val Gln Glu Ala Glu Leu Arg Arg Gln Thr
210                 215                 220

Val Ile Gln Tyr Ser Pro Glu His Pro Gln Ala Gln Glu Tyr Arg Asp
225                 230                 235                 240

Leu Gly Asp Lys Ile Val Asn Asn Thr Lys Leu Thr Ile Pro Thr Pro
                245                 250                 255

Ile Asp Asn Asp Glu Leu Glu Glu Leu Leu Ile Asn Tyr Gly Leu Leu
            260                 265                 270

Gly Ser Glu Glu Glu Tyr Lys Lys Val Met Glu Ala Asp Met Ala Ala
        275                 280                 285

Gln Ala Leu Thr Arg Gly Ala Lys
    290                 295
```